(12) United States Patent
Albanese et al.

(10) Patent No.: US 11,738,161 B2
(45) Date of Patent: Aug. 29, 2023

(54) SYSTEM AND METHOD FOR ADAPTIVE SCHEDULING OF PAUSE MANEUVERS USED FOR ESTIMATION OF COMPLIANCE AND/OR RESISTANCE DURING MECHANICAL VENTILATION

(71) Applicant: KONINKLIJKE PHILIPS N.V., Eindhoven (NL)

(72) Inventors: Antonio Albanese, Mission Viejo, CA (US); Francesco Vicario, Boston, MA (US); Caitlyn Marie Chiofolo, New Hyde Park, NY (US); Nicolas Wadih Chbat, White Plains, NY (US); Fernando Jose Isaza, Carlsbad, CA (US); Smita Garde, Irvine, CA (US); Daniel Van Hise, Dover, NH (US); Adam Jacob Seiver, Los Altos Hills, CA (US)

(73) Assignee: Koninklijke Philips N.V., Eindhoven (NL)

( * ) Notice: Subject to any disclaimer, the term of this patent is extended or adjusted under 35 U.S.C. 154(b) by 605 days.

(21) Appl. No.: 16/478,022

(22) PCT Filed: Jan. 12, 2018

(86) PCT No.: PCT/EP2018/050774
§ 371 (c)(1),
(2) Date: Jul. 15, 2019

(87) PCT Pub. No.: WO2018/130658
PCT Pub. Date: Jul. 19, 2018

(65) Prior Publication Data
US 2020/0121877 A1 Apr. 23, 2020

Related U.S. Application Data

(60) Provisional application No. 62/446,644, filed on Jan. 16, 2017.

(51) Int. Cl.
*A61M 16/00* (2006.01)
*A61M 15/00* (2006.01)
(Continued)

(52) U.S. Cl.
CPC ........ *A61M 16/024* (2017.08); *A61M 15/002* (2014.02); *A61M 16/0003* (2014.02); *A61M 16/202* (2014.02); *G06F 17/18* (2013.01); *A61M 2016/0027* (2013.01); *A61M 2016/0033* (2013.01); *A61M 2205/3327* (2013.01); *A61M 2205/3334* (2013.01); *A61M 2230/46* (2013.01)

(58) Field of Classification Search
CPC .............. A61M 16/024; A61M 15/002; A61M 16/0003; A61M 2205/3334; A61M 2230/46; A61B 5/087
See application file for complete search history.

(56) References Cited

U.S. PATENT DOCUMENTS

| 5,876,352 A | 3/1999 | Weismann |
| 5,884,622 A | 3/1999 | Younes |

(Continued)

FOREIGN PATENT DOCUMENTS

WO    WO2016098020 A1    6/2016

OTHER PUBLICATIONS

PCT International Search Report, International application No. PCT/EP2018/050774, dated May 8, 2018.

(Continued)

*Primary Examiner* — Philip R Wiest
*Assistant Examiner* — Sarah B Lederer
(74) *Attorney, Agent, or Firm* — Daniel H. Brean (57) ABSTRACT

A ventilation device includes a mechanical ventilator (10), respiratory sensors (30, 32) configured to acquire measurements of respiratory variables including at least measurements of airway pressure and airway flow, and an electronic processor (14) programmed to perform a ventilation method including: operating the mechanical ventilator to provide mechanical ventilation controlled using measurements (Continued)

acquired by the respiratory sensors; performing a pause maneuver comprising closing at least one of an inhalation valve (38) and an exhalation valve (40) for a pause interval and estimating a respiratory mechanics index from one or more respiratory system parameters estimated from measurements acquired by the respiratory sensors during or after the pause interval; and triggering a pause maneuver in response to detecting a change in the estimated respiratory mechanics index.

8 Claims, 3 Drawing Sheets

(51) Int. Cl.
*A61M 16/20* (2006.01)
*G06F 17/18* (2006.01)

(56) References Cited

U.S. PATENT DOCUMENTS

| | | | |
|---|---|---|---|
| 6,390,091 | B1 | 5/2002 | Banner |
| 8,424,521 | B2 | 4/2013 | Jafari |
| 8,728,002 | B2 * | 5/2014 | Al-Rawas ............ A61B 5/087 600/533 |
| 2007/0272241 | A1 * | 11/2007 | Sanborn ............ A61M 16/024 128/204.23 |
| 2010/0236553 | A1 * | 9/2010 | Jafari ............... A61M 16/0875 128/204.21 |
| 2014/0048072 | A1 * | 2/2014 | Angelico ............ A61M 16/026 128/204.23 |

OTHER PUBLICATIONS

Al-Rawas N. et al., "Expiratory Time Constant for Determinations of Plateau Pressure, Respiratory System Compliance, and Total Resistance", BioMed Central Ltd., 17:R23, pp. 2-11, 2013.

Gould et al: "Principles of Artificial Ventilation", Mar. 1, 2004, vol. 5, No. 3, Mar. 1, 2004 (Mar. 1, 2004), pp. 71-80, XP005770274.

Chatburn R L: "Classification of Mechanical Ventilators", May 1, 1994 (May 1, 1994), Principles and Practice of Mechanical Ventila, McGraw-Hill Professional Publishing, US, pp. 37-64, XP008108813.

"Medical Electrical Equipment—Part 2-12: Particular Requirements for Basic Safety and Essential Performance of Critical Care Ventilators", ISO 80601-2-12:2011, IEC, 3, Rue De Varembé, PO Box 131, CH-1211 Geneva 20, Switzerland, May 23, 2011 (May 23, 2011), pp. 1-78, XP082004329.

* cited by examiner

SYSTEM AND METHOD FOR ADAPTIVE SCHEDULING OF PAUSE MANEUVERS USED FOR ESTIMATION OF COMPLIANCE AND/OR RESISTANCE DURING MECHANICAL VENTILATION

CROSS-REFERENCE TO RELATED APPLICATIONS

This patent application claims the priority benefit under 35 U.S.C. § 371 of international patent application no. PCT/EP2018/050774, filed Jan. 12, 2018, claims the priority benefit under 35 U.S.C. § 119(e) of U.S. Provisional Application No. 62/446,644 filed on Jan. 16, 2017, the contents of which are herein incorporated by reference.

BACKGROUND

Measurement of respiratory parameters of a mechanically ventilated patient, including the lung compliance C (or, equivalently, lung elastance E=1/C) and lung resistance R, is useful for numerous purposes. For example, these values can be used to tailor ventilation strategy, and are informative for selecting specific ventilator settings. In some ventilator modes, it may also be useful to estimate the patient's respiratory effort, usually characterized by a respiratory muscle pressure $P_{mus}(t)$ which varies as a function of time (t) over a patient breath. $P_{mus}(t)$ rapidly increases in magnitude at onset of inspiration (i.e. inhalation) and usually remains positive over the inspiration period, and then falls to zero at the transition from inspiration to expiration (or exhalation; note that inspiration and inhalation are used interchangeably herein, and likewise expiration and exhalation are used interchangeably herein). The transition to zero at the inspiration/expiration transition can be complex due to respiratory muscle recoil-generated pressure or other complicating phenomena. As a practical example, in the mechanical respiration mode known as Proportional Assist Ventilation (PAV), the respirator acts as an amplifier of the patient's respiratory effort, and hence uses the measured $P_{mus}(t)$. In other modes such as Pressure Support Ventilation (PSV), knowledge of $P_{mus}(t)$ can be used to tune the supporting positive pressure provided by the mechanical ventilation.

For a passive patient who is not providing respiratory effort (that is, for which $P_{mus}(t)=0$ for all t), the Equation of Motion of the Lungs can be used to determine R and C from measurements of airway pressure P(t), lung air flow Q(t), and lung volume V(t) (computed as a time integral of Q(t)). For an actively breathing patient, however, $P_{mus}(t)$ is not zero, which complicates evaluation of R and C. An end-inspiration pause maneuver is a known approach for measuring respiratory parameters in an actively breathing patient. In this pause maneuver, the inhalation and exhalation valves are closed for a time interval at around the transition from completion of inhalation to the start of exhalation, so that no air can leave the lungs. This allows the lung pressure to equilibrate, permitting assessment of the respiratory compliance C.

In ventilation strategies that employ pause maneuvers to estimate respiratory parameters such as respiratory compliance, the pause maneuver is typically performed at regular intervals of a certain number of breaths. In a variant approach, it is known to perform pause maneuvers at random intervals of 4-10 breaths. See Sanborn et al., U.S. Pub. No. 2007/0272241 A1. Randomization is done to reduce the likelihood of the patient becoming familiarized with the pause maneuver interval and consciously or unconsciously altering the respiratory effort during the breaths that include a pause maneuver. Id.

The following discloses new and improved systems and methods.

BRIEF SUMMARY

In one disclosed aspect, a ventilation device comprises: a mechanical ventilator; respiratory sensors configured to acquire measurements of respiratory variables including at least measurements of airway pressure and airway flow; an electronic processor; and a non-transitory storage medium storing instructions readable and executable by the electronic processor to perform a ventilation method. The method includes: operating the mechanical ventilator to provide mechanical ventilation controlled using measurements acquired by the respiratory sensors; performing a pause maneuver comprising closing at least one of an inhalation valve and an exhalation valve for a pause interval and estimating a respiratory mechanics index from one or more respiratory system parameters estimated from measurements acquired by the respiratory sensors during or after the pause interval; and triggering a pause maneuver in response to detecting a change in the estimated respiratory mechanics index. In one non-limiting illustrative example, the respiratory mechanics index is estimated by computing a time constant of a decay of airway flow measured by the respiratory sensors during an exhalation phase of a breath, and a change in the estimated respiratory mechanics index is detected as a detected change in the time constant computed over successive breaths. In another non-limiting illustrative example, respiratory resistance and respiratory compliance or elastance are estimated for successive breaths based on airway flow and airway pressure measured by the respiratory sensors, and the respiratory mechanics index is estimated by performing Bayesian modeling of the estimated respiratory resistance and the respiratory compliance or elastance to generate a respiratory resistance probability density function and a respiratory compliance or elastance probability density function. In this example, a change in the estimated respiratory mechanics index is detected as a detected broadening of at least one of the respiratory resistance probability density function and the respiratory compliance or elastance probability density function.

In another disclosed aspect, a non-transitory storage medium stores instructions readable and executable by an electronic processor to perform operations including: operating a mechanical ventilator to provide mechanical ventilation; performing a pause maneuver comprising closing at least one of an inhalation valve and an exhalation valve of the mechanical ventilator for a pause interval and estimating one or more respiratory system parameters from airway flow and airway pressure measurements acquired by respiratory sensors during or after the pause interval; monitoring an estimated respiratory mechanics index based on at least one of airway flow and airway pressure measured by respiratory sensors over successive breaths; and triggering a pause maneuver in response to detecting a change in the estimated respiratory mechanics index over successive breaths.

In another disclosed aspect, a ventilation method includes: operating a mechanical ventilator to provide mechanical ventilation; estimating a respiratory mechanics index over successive breaths during the operating; detecting a change in the estimated respiratory mechanics index; and triggering a pause maneuver in response to the detected change in the estimated respiratory mechanics index, the pause maneuver comprising closing at least one of an inhalation valve and an exhalation valve of the mechanical ventilator for a pause interval and estimating respiratory compliance from airway measurements acquired during or after the pause interval. The estimating, detecting, and triggering is performed by an electronic processor.

One advantage resides in reduced patient discomfort due to frequent pause maneuvers performed during mechanical ventilation.

Another advantage resides in reduced interference with the patient's normal breathing cycle due to frequent pause maneuvers performed during mechanical ventilation.

Another advantage resides in providing more accurate and consistent values for respiratory parameters, e.g. resistance R and compliance C (or elastance E).

Another advantage resides in providing reduced usage wear on mechanical respirator components.

Another advantage resides in providing mechanical ventilation with improved therapeutic efficiency.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Sanborn et al., U.S. Pub. No. 2007/0272241 A1 discloses an approach in which pause maneuvers are applied at random intervals of 4-10 breaths, to combat the tendency that the patient may consciously or unconsciously alter his or her breathing in anticipation of a pause maneuver. However, there is a disadvantage of this approach. The observation that the patient may consciously or unconsciously alter a breath in anticipation of a pause maneuver implies that the pause maneuvers discomfort or disturb the patient (in the case of conscious breathing adjustment) or interfere with the patient's normal breathing cycle (in the case of unconscious breathing adjustment).

It is further recognized herein that performing the pause maneuver at intervals of 4-10 breaths (on average) is unnecessarily frequent. For a typical adult respiratory rate of 12-20 breaths per minute, intervals of 4-10 breaths corresponds to performing a pause maneuver once to several times each minute. However, respiratory compliance (or elastance) and respiratory resistance do not typically change at such a short time scale. Rather, these respiratory parameters usually change more slowly, due to effects such as fatigue of the thoracic diaphragm and/or chest wall muscles, gradual build-up of fluid in the lungs, phlegm buildup partially occluding the trachea and/or bronchial tubes, gradual onset of pneumonia or some other gradual medical change, or so forth. More rapid changes in respiratory parameters may occur, but these are usually attributable to discrete occurrences, e.g. shifting of an endotracheal tube, volitional patient movement, sudden onset of an acute medical condition, an identifiable treatment operation such as initiating, terminating, or otherwise changing the flow of an aerosolized medication, or so forth. Such discrete occurrences are usually infrequent, and hence represent isolated "step" changes in the respiratory system parameters.

As still further recognized herein, frequent pause maneuvers have certain potential disadvantages, such as introducing noise in the estimated respiratory resistance and/or compliance (or elastance), and compromised therapeutic efficiency of the mechanical ventilation due to the frequent insertion of unnecessary pause maneuvers that interrupt the normal ventilation.

In view of the foregoing, approaches are disclosed herein which enable a substantial reduction in the frequency of pause maneuvers while retaining the ability of the pause maneuver strategy to effectively track actual changes in respiratory system parameters. In the disclosed approaches, a respiratory mechanics index is estimated over successive breaths during the mechanical ventilation. A pause maneuver is performed in response to a detected change in the estimated respiratory mechanics index. The pause maneuver usually entails closing the inhalation valve and/or the exhalation valve of the mechanical ventilator for a pause interval, and estimating one or more respiratory parameters (e.g. compliance/elastance and/or resistance) from airway measurements acquired during or after the pause interval.

In this pause maneuver triggering paradigm, various approaches can be used for estimating the respiratory mechanics index. In one approach, a time constant of decay of airway flow measured by the respiratory sensors during the exhalation phase is monitored for each breath, and a change in estimated respiratory mechanics index is detected as a detected change in the time constant computed over successive breaths. In another approach, a non-pause-based estimate of a respiratory parameter (e.g. respiratory resistance and/or respiratory compliance or elastance) is performed under a (possibly unrealistic) assumption that no respiratory muscle pressure is being applied, and a change in estimated respiratory mechanics index is detected as a detected change in the estimated at least one respiratory parameter.

In both these approaches (monitoring the expiration time constant or monitoring a respiratory parameter estimated under the assumption of no respiratory muscle pressure) the resulting value is not necessarily clinically useful per se. For example, compliance estimated under the untested assumption of no respiratory muscle pressure may be of limited accuracy for an actively breathing patient. The expiration time constant conflates resistance and compliance, making its clinical interpretation difficult. However, the purpose of these values is only to assess respiratory mechanics variations. In this context, a change in the time constant or the non-pause-based respiratory parameter estimate indicates some change in respiratory mechanics—and this change, whatever its cause, motivates the triggering of a pause maneuver to (more accurately) reassess the respiratory parameters.

In a variant embodiment, a non-pause-based estimate of respiratory resistance and respiratory compliance or elastance is performed for successive breaths based on airway flow and airway pressure measured by the respiratory sensors (for example, again assuming no respiratory muscle effort on the part of the patient), and Bayesian modeling of the estimated respiratory resistance and the estimated respiratory compliance or elastance is performed to generate a respiratory resistance probability density function and a respiratory compliance or elastance probability density function. In the case of stable respiration, these distributions should be relatively narrow; on the other hand, a change in respiratory mechanics should be reflected in a broadening of the distribution, at least until a new stable respiratory state is reached at which point the distribution should again narrow. In these embodiments, a change in estimated respiratory mechanics index is detected as a detected broadening of at least one of the respiratory resistance probability density function and the respiratory compliance or elastance probability density function, and a pause maneuver is triggered by such detection.

The respiratory mechanics index estimate can also in some embodiments be based on non-respiratory data. For example, a change in estimated respiratory mechanics index may be detected as a detected change in flow of an aerosolized medication delivered by a nebulizer, under the expectation that a change in aerosolized medication influx may alter respiratory resistance and/or compliance/elastance.

In some embodiments, a pause maneuver may also be triggered under certain circumstances by something other than detection of respiratory mechanics changes. For example, in some embodiments, if the number of breaths (or a time interval) since the last pause maneuver exceeds some maximum value then this triggers a pause maneuver. This optional variant ensures that pause maneuvers are performed at least occasionally—but the maximum number of breaths between pause maneuvers (or the time interval) can be large, e.g. a few dozen or few hundred breaths, or a time interval of minutes to tens of minutes in some non-limiting contemplated implementations.

The disclosed approaches for triggering pause maneuvers on the basis of detected changes in respiratory mechanics index may in generally be employed in conjunction with substantially any ventilation mode, e.g. (by way of non-limiting illustration) with a pressure support ventilation (PSV) mode, a proportional assists ventilation (PAV) mode, a synchronized intermittent mandatory ventilation (SIMV) mode, a pressure controlled ventilation (PCV) mode, or a volume controlled ventilation (VCV) mode. The approaches are particularly useful in the context of ventilation modes that are commonly used for actively breathing patients, such as a PSV mode or a PAV mode.

Figure 1:
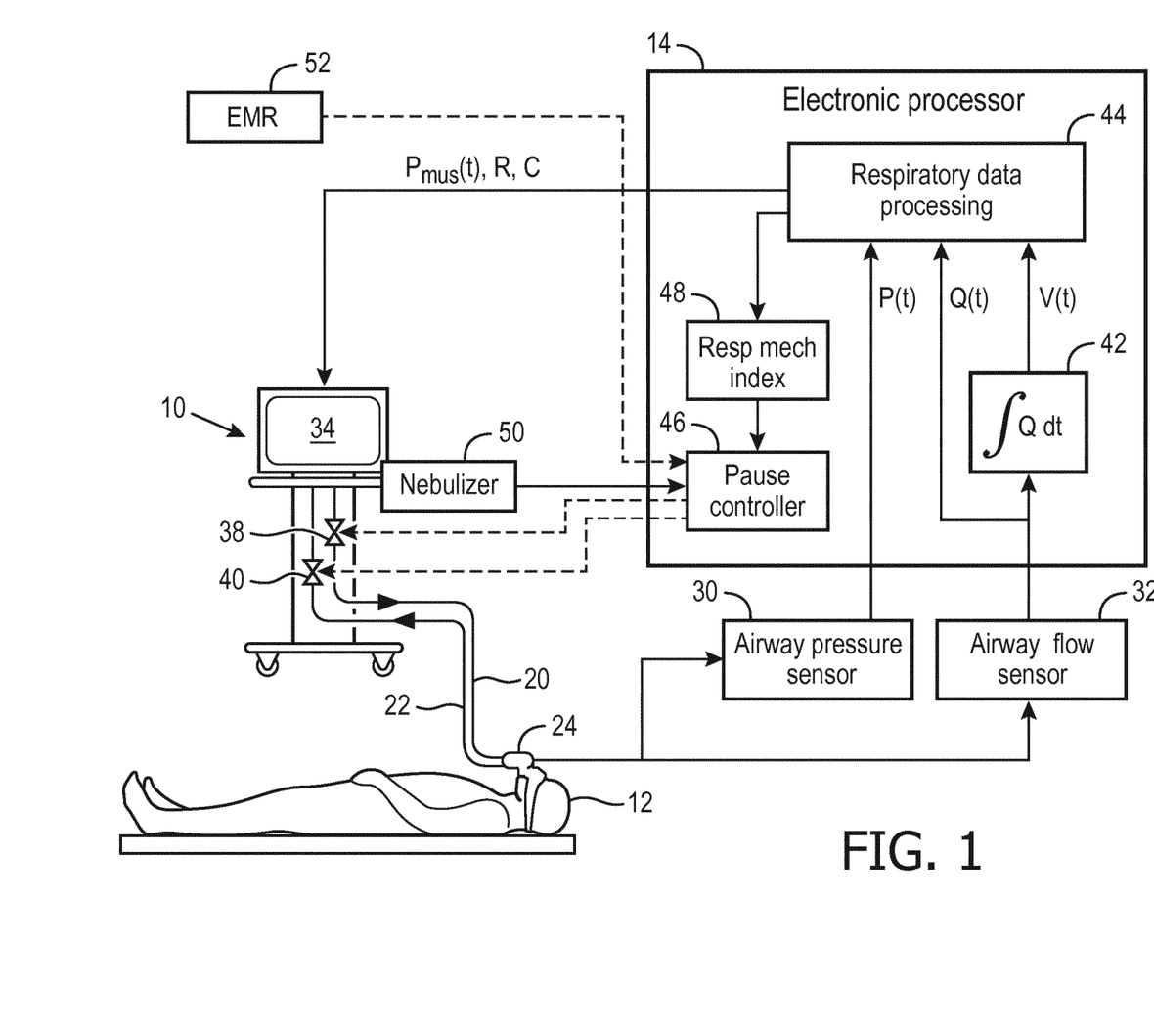
FIG. 1 diagrammatically illustrates a mechanical ventilation device.

With reference to FIG. 1, some illustrative embodiments of the disclosed approaches for triggering pause maneuvers on the basis of detected changes in respiratory mechanics index are described. As diagrammatically shown in FIG. 1, a ventilation device includes a mechanical ventilator 10 that delivers therapeutic ventilation to a patient 12. An electronic processor 14 (which may be integral with the mechanical ventilator 10 or with some other electronic component) performs respiratory data processing as disclosed herein. The ventilator 10 is connected with the patient 12 via an inlet air hose 20 and an exhaust air hose 22. The interface with the patient's respiratory system is via a non-invasive face mask 24, as illustrated, or alternatively may be via an invasive endotracheal tube (not shown). Suitable sensors including an illustrative airway pressure sensor 30 and an illustrative airway flow sensor 32 are provided to monitor the patient's respiration. These respiratory sensors 30, 32 may be variously embodied and/or referred to by various nomenclature, e.g. as a pneumograph, pneumotachograph, as separate discrete flow and pressure sensors, or so forth. While the respiratory sensors 30, 32 are diagrammatically illustrated in FIG. 1, it will be appreciated that these sensors 30, 32 may be variously embodied, e.g. as components integral with the face mask 24, or located inside the housing of the mechanical ventilator 10, or mounted externally on the air hoses 20, 22, or so forth. The sensors 30, 32 may have any practical configuration, e.g. in-line sensors, side-stream sensors, or so forth. In addition to the illustrative sensors 30, 32, other respiratory sensors may be provided such as a capnography, and the patient 12 may be monitored by other physiological sensors (not shown), e.g. to monitor heart rate, blood pressure, $SpO_2$, or so forth. The illustrative mechanical ventilator 10 includes a display 34 typically providing display of the various measurements such as airway pressure denoted herein as P(t), measured using the airway pressure sensor 30, airway flow denoted herein as Q(t) measured using the airway flow sensor 32, and optionally other measured parameters (pulse, $SpO_2$, $CO_2$ measured by a capnography, et cetera). In the illustrative examples, the airway pressure sensor 30 is located at the patient port (e.g. tracheal tube or respiratory mask) so as to directly measure the airway pressure P(t), and likewise the airway flow sensor 32 is located at the patient port to directly measure the airway air flow Q(t). More generally, the airway pressure sensor 30 may be any sensor that is used to estimate the airway pressure P(t), e.g. the airway pressure sensor 30 may as a further illustration be a pressure sensor located elsewhere in the respiratory circuit (i.e. not at the patient port) that measures a pressure from which the airway pressure P(t) can be reliably estimated, e.g. based on a known flow resistance between the patient port and the measurement point. Likewise, the airway flow sensor 32 may be any sensor that is used to estimate the airway flow Q(t), e.g. the airway flow sensor 32 may as a further illustration be a flow sensor located elsewhere in the respiratory circuit that measures a flow from which the airway air flow Q(t) can be reliably estimated. In the following, the term "measured" with be used in conjunction with P(t) and Q(t) but it is to be understood that more generally these values may be estimated from measurements of other associated quantities. These may be displayed as numbers, trend lines, and/or so forth. The display 34 may also serve as a user interface, e.g. including touch-screen input capability or having auxiliary user input devices (not shown) such as a physical keyboard, trackball, or so forth. As a user interface, the display 34 may display information such as the fraction of inspired oxygen ($FiO_2$) controlled by the setting of an oxygen canister, the preset pressure of pressure-controlled breaths delivered to the patient 12 by the ventilator 10 in accord with a chosen ventilator mode such as Pressure Support Ventilation (PSV) mode, Pressure Control Ventilation (PCV), or another pressure-based ventilation mode. Other salient information for monitoring the mechanical ventilation and the status of the patient 12 may also/alternatively be displayed on the display 34 of the mechanical ventilator 10.

As is typical for mechanical ventilator devices, an inspiration valve 38 and an expiration valve 40 are also provided. The inspiration and expiration valves 38, 40 are mounted in-line on the respective inlet and exhaust air hoses 20, 22, but other configurations are contemplated, e.g. these valves may be mounted as components inside the housing of the mechanical ventilator 10, or may be integral with the face mask 24. To ensure proper flow direction through the ventilation circuit, in a typical valve operational scheme during inhalation the inhalation valve 38 is open and the expiration valve 40 is closed; while during expiration the inhalation valve 38 is closed and the expiration valve 40 is open.

In some suitable embodiments, the electronic processor 14 is a microprocessor or microcontroller operatively connected with auxiliary components (not shown) including a non-transitory storage medium storing instructions readable and executable by the electronic processor. The non-transitory storage medium may, for example, comprise one or more of a read-only memory (ROM), electronically erasable programmable read-only memory (EEPROM), flash memory, or other electronic memory; a disk drive or other magnetic memory; an optical disk or other optical memory; or so forth. The auxiliary components may further include interfacing components for generating and outputting control signals for controlling the mechanical ventilator 10, sensor couplings or input interfaces for reading measurements output by the sensors 30, 32, and so forth. As previously mentioned, the electronic processor 14 may be integral with and disposed inside the housing of the mechanical ventilator 10 (e.g. the electronic processor 14 may be the electronics or electronic controller of the ventilator 10), or may be the processor of a separate component such as a computer (not shown). The electronic processor 14 is programmed via instructions stored on the non-transitory storage medium to perform various functions. If the electronic processor 14 is the controller of the mechanical ventilator 10 then the electronic processor 14 is suitably programmed to operate the mechanical ventilator 10 to perform therapeutic ventilation in accord with a chosen ventilation mode (e.g. PSV or PAV), as well as to receive sensor data from the sensors 30, 32 and to display the sensor data and salient ventilator data on the display 34.

The electronic processor 14 is programmed to receive or estimate airway flow measurements Q(t) from the airway flow sensor 32 and to perform an integration process 42 to time-integrate the airway flow measurements to compute the lung volume V(t)=∫Q(t)dt where t denotes time and the integral is from a defined start time, e.g. starting at the start of inhalation. It will be appreciated that in some embodiments this integration is performed via some other processor and the result V(t) then input to the electronic processor 14—for example, the airway flow sensor 32 may include such an electronic processor programmed to perform the integration process 42 so that the airway flow sensor is a combined air flow/air volume sensor.

The electronic processor 14 is further programmed to perform various types of respiratory data processing 44. This may entail, for example, detecting alert conditions (overpressure, large air leak, or so forth), computing respiratory variables such as positive end-expiratory pressure (PEEP), end-tidal $CO_2$ (if receiving capnography data), or so forth. The electronic processor 14 is further programmed to perform a pause maneuver by implementing a pause controller 46 that executes a pause by closing the inhalation valve 38 and/or the exhalation valve 40 for a pause interval and acquiring measurements using the respiratory sensors 30, 32 during or after the pause interval. The pause interval is typically short, e.g. on the order of 0.5 seconds or less, and in some embodiments in the range of a few hundred milliseconds. The respiratory data processing 44 then includes computing one or more respiratory system parameters from measurements acquired by the respiratory sensors during or after the pause interval. For example, a formulation of the Equation of Motion of the Lungs can be written as:

$$P(t) = R \cdot Q(t) + \frac{1}{C} \cdot V(t) + P_{mus}(t) \tag{1}$$

where, as previously defined, R is the respiratory resistance, C is the respiratory compliance, V(t) is the lung volume, Q(t) is the measured airway air flow, P(t) is the measured airway pressure, and $P_{mus}(t)$ is the respiratory muscle pressure. If the respiratory muscle pressure $P_{mus}(t)$ is assumed to be zero then Equation (1) reduces to:

$$P(t) = R \cdot Q(t) + \frac{1}{C} \cdot V(t) \tag{2}$$

During the pause maneuver with both inspiration and expiration valves 38, 40 closed, V(t) is a constant, Q(t) is zero. If the pause is performed after end of inspiration and after settling of any respiratory muscle recoil-generated pressure then $P_{mus}(t)$ is also zero, leading to:

$$P = \frac{1}{C} \cdot V \rightarrow C = \frac{V_T}{P_{plat} - PEEP} \tag{3}$$

In Equation (3), $V_T$ is the tidal volume during the pause, and can be computed from the integral V(t)=∫Q(t)dt over the breath up to the pause. PEEP is the Peak End-Expiratory Pressure, i.e. the "baseline" pressure at the end of the expiratory period, and $P_{plat}$ is the "plateau" airway pressure P(t) measured during the pause, after settling of any respiratory muscle recoil pressure. In general, $P_{plat}$ should be measured when the flow into the lung is zero. The pause duration should be long enough so this condition is achieved as it implies muscle activity otherwise. With C thus estimated, R can be computed from Equation (2) using (P(t),Q(t)) measurements during the expiration period, assuming $P_{mus}(t)=0$ which is usually the case during expiration.

The respiratory parameters, e.g. resistance R and compliance C or elastance E, estimated via the pause maneuver, may be used in various ways. For example, these values may be displayed on the display 34 of the mechanical ventilator 10 as real-time numeric values and/or as trend lines (e.g. R versus time and C versus time). These values may be useful information for medical personnel assessing the patient's condition and making clinical decisions such as whether the patient can be safely weaned off the ventilator 10. Additionally or alternatively, the mechanical ventilation provided by the mechanical ventilator 10 may be controlled using the one or more respiratory system parameters estimated from measurements acquired by the respiratory sensors 30, 32 during or after the pause interval. For example, with the values of R and C estimated by the pause maneuver (and possibly a value for PEEP estimated by an end-expiratory pause maneuver), Equation (1) can be solved for $P_{mus}(t)$.

As further indicated in FIG. 1, the pause maneuver is triggered by the pause controller 46 based on a detected change in respiratory mechanics as measured by a respiratory mechanics index 48. The respiratory mechanics index may, as previously mentioned, be a time constant of the decay of airway air flow Q(t) during the expiration period, or may be the value of one or more respiratory parameters (e.g. R and/or C or E) estimated from Equation (2) with $P_{mus}(t)$ assumed to be zero, or so forth. In some embodiments, the pause controller 46 may trigger a pause maneuver in response to a change in some other input, such as a change in flow of an aerosolized medication delivered by a nebulizer 50. Optionally, the nebulizer 50 may be integral with the mechanical ventilator 10 as shown in FIG. 1, so that the nebulizer flow setting is directly available to the ventilator 10 and hence to the processor 14 in embodiments in which the processor 14 comprises the controller of the ventilator 10. The change in flow sufficient to trigger a pause maneuver may, for example, be the initiation of flow of an aerosolized medication, or the termination of such flow. In some embodiments, a sufficient change in flow to trigger a pause maneuver may be a change in the rate of flow, rather than the starting/stopping of such flow. As further indicated in FIG. 1, in some embodiments the pause controller 46 may trigger a pause maneuver in response to other data such as a change in the patient's heart rate (or blood pressure, or other vital sign) of greater than some threshold percentage. In some cases, such vital sign data may be directly available to the ventilator 10, e.g. if the ventilator includes or is connected with a heart rate monitor. In other cases, the vital sign data may be obtained from a patient monitor, an Electronic Medical Record (EMR) 52, which is also sometimes known in the art by other nomenclature, e.g. an Electronic Health Record (EHR), accessed via a wired or wireless medical data network (e.g. Ethernet, WiFi), or so forth.

Figure 2:
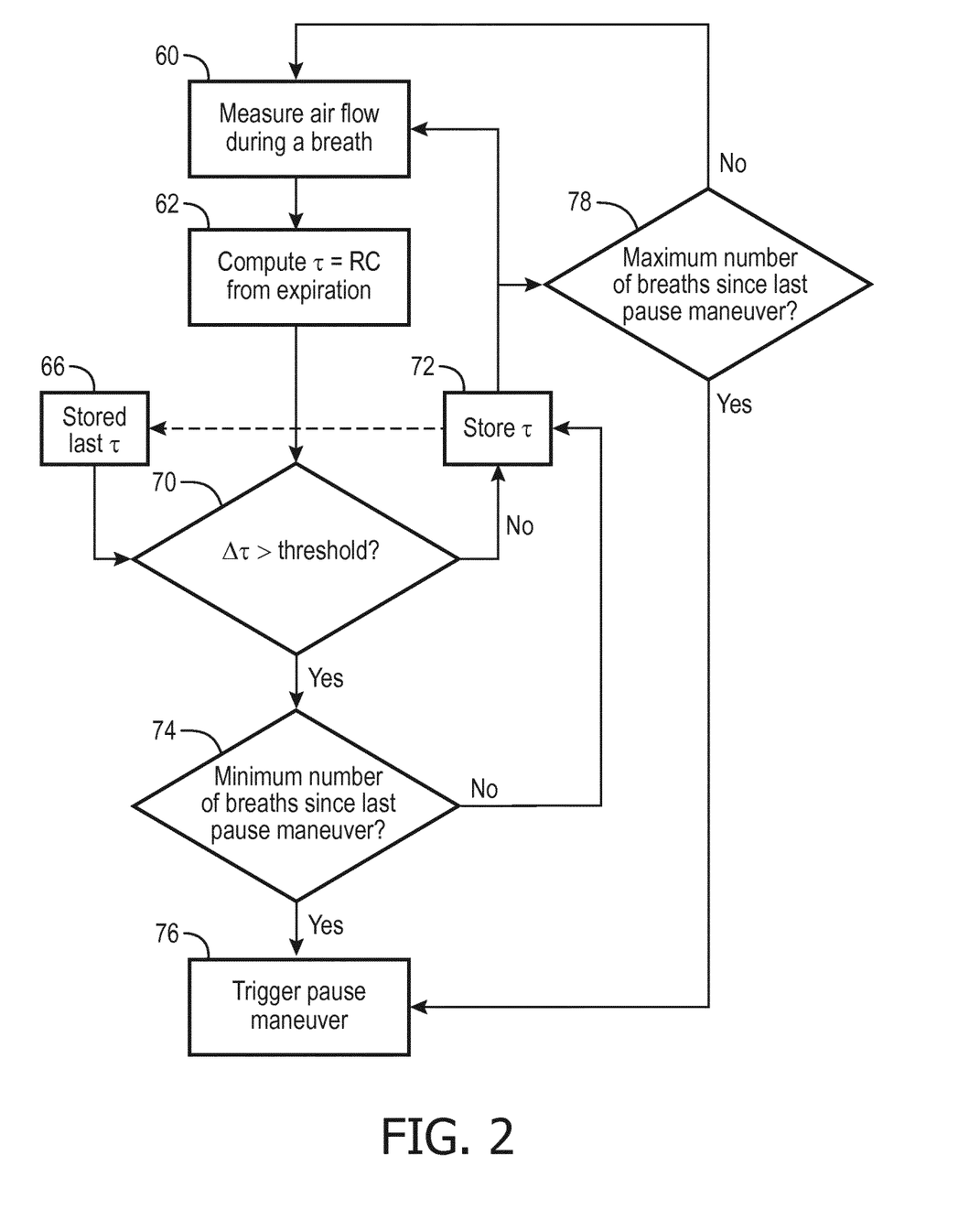
FIG. 2 shows a flow chart of a process for triggering pause maneuvers based on a measured time constant $\tau=RC$ where R is respiratory system resistance and C is respiratory system compliance.

With reference to FIG. 2, process flow of the ventilation device of FIG. 1 in the case in which the respiratory mechanics index 48 is a time constant of the decay of air flow Q(t) during expiration is described. In an operation 60, air flow is measured during a breath. In an operation 62, the time constant, denoted herein as $\tau$, is computed. In general, this time constant is $\tau = RC$ where R is the respiratory resistance and C is the respiratory compliance. (Alternatively, this can be written as $\tau = R/E$ where $E = 1/C$ is the respiratory elastance).

One suitable approach for computing $\tau$ is as follows. The airway pressure and flow data for a generic breath can be described via the following equation (a variant of the Equation of Motion of the Respiratory System of Equation (1)):

$$P(t) = RQ(t) + E[V(t) - V(0)] + P_{mus}(t) + P_0 \quad (4)$$

where V(0) is the volume of air contained in the lungs at time t=0, P(t) is the pressure at the airway opening, Q(t) is the air flow into and out of the patient's lungs, V(t) is the volume of air contained in the lungs, $P_{mus}(t)$ is the respiratory muscles pressure, $P_0$ is a constant term used to balance the equation at time t=0, R is the respiratory system resistance, and E is the respiratory system elastance (inverse of the respiratory system compliance C). The starting point of the breath (t=0) is chosen to coincide with the time at which $P_{mus}(t)$ starts decreasing from baseline zero value indicating the onset of patient's inspiratory effort. Note that in general, the flow at time t=0 (Q(0)) can be different than zero (negative) if intrinsic positive end-expiratory pressure, i.e. PEEP (PEEPi), is developed. In the remaining, it is assumed that this is the case, but the method can be extended without loss of generality to the cases where PEEPi is not present by assuming that Q(0)=0.

Since volume cannot be directly measured, it is convenient to express the term V(t)−V(0) in Equation (4) via the corresponding flow integral:

$$P(t) = RQ(t) + E\int_0^t Q(\tau)d\tau + P_{mus}(t) + P_0 \quad (5)$$

During exhalation, the respiratory muscles are most likely relaxed. Accordingly, $P_{mus}(t) = 0$ and Equation (5) becomes:

$$P(t) = RQ(t) + E\int_0^t Q(\tau)d\tau + P_0 \quad (6)$$

Equation (5) evaluated at time t=0 yields:

$$P(0) = RQ(0) + P_{mus}(0) + P_0 \quad (7)$$

Since we have chosen $P_{mus}(0) = 0$ a value for $P_0$ can be computed from Equation (7) as:

$$P_0 = P(0) - RQ(0) \quad (8)$$

Plugging into Equation (6) the definition of $P_0$ from Equation (8), we obtain:

$$P(t) = RQ(t) + E\int_0^t Q(\tau)d\tau + P(0) - RQ(0) \quad (9)$$

and $$P(t) - P(0) = R(Q(t) - Q(0)) + \int_0^t Q(\tau)d\tau \quad (10)$$

During exhalation, the mechanical ventilator 10 is controlled to provide, after some time from cycling off, a constant positive-end expiratory pressure (PEEP) until a new breath initiates. Therefore, by definition, P(t)=P(0) and Equation (10) becomes:

$$0 = R(Q(t) - Q(0)) + E\int_0^t Q(\tau)d\tau \quad (11)$$

which can be solved for the respiratory time constant $\tau = R/E$ to yield:

$$\tau = -\frac{\int_0^t Q(\tau)d\tau}{Q(t) - Q(0)} \quad (12)$$

Note that Equation (12) is valid for all the time samples during exhalation at which the mechanical ventilator 10 is providing the set PEEP (P(t)=PEEP). So, it can be applied at multiple time samples and an estimate of the time constant $\tau$ can be found via least-squares or other methods (e.g. median, average). Though not required, it may be advantageous to use data between a sample right after the point at which maximum expiratory flow occurs (e.g. Flow=80% of Peak Expiratory Flow, provided that P(t)=PEEP already) and a sample right before flow becomes negligible (e.g. Flow=30% of Peak Expiratory Flow).

With continuing reference to FIG. 2, after the decay time constant $\tau$ of the air flow Q(t) during expiration has been computed, e.g. according to Equation (12), in an operation 70 the value of $\tau$ for the current breath is compared with the stored last value of $\tau$ 66. The comparison may be expressed as an absolute value of the difference, or as a percentage of this absolute difference, e.g.:

$$\Delta\tau = \frac{|\tau(n) - \tau(n-1)|}{\frac{1}{2}(\tau(n) + \tau(n-1))} \quad (13)$$

where $\tau(n)$ is the time constant for the current breath and $\tau(n-1)$ is the time constant 66 for the last breath. In the operation 70, if $\Delta\tau$ is greater than a threshold then this is deemed to be a change in respiratory mechanics. The threshold for the detected change $\Delta\tau$ in the time constant over successive breaths to trigger a pause maneuver may be optimized empirically using mechanical ventilation data for a training set of past patients. If the change in time constant $\Delta\tau$ does not meet the threshold then flow passes to a block 72 where the time constant $\tau(n)$ is stored as the last time constant value (written another way, $\tau(n-) \leftarrow \tau(n)$) and flow passes back to block 60 to measure the time constant for the next breath.

On the other hand, if the comparison 70 finds that Δτ is greater than the threshold then this is deemed to be a change in respiratory mechanics sufficient to trigger a pause maneuver. In the illustrative example of FIG. 2, a further test 74 is performed, at which if a minimum number of breaths has not occurred since the last pause maneuver then the next pause maneuver is delayed, i.e. flow passes to block 72 as just described. This optional test 74 ensures that pause maneuvers are not performed for every breath, e.g. in some embodiments the minimum number of breaths between pause maneuvers may be set to four. Assuming both tests 70, 74 are passed, then in an operation 76 a pause maneuver is triggered.

Another illustrated variant is that in an operation 78, if a maximum number of breaths has occurred since the last pause maneuver than flow automatically passes to block 76 to trigger a new pause maneuver. This optional operation 78 ensures that pause maneuvers are performed occasionally even if the time constant τ remains constant (within the threshold employed in operation 70).

Figure 3:
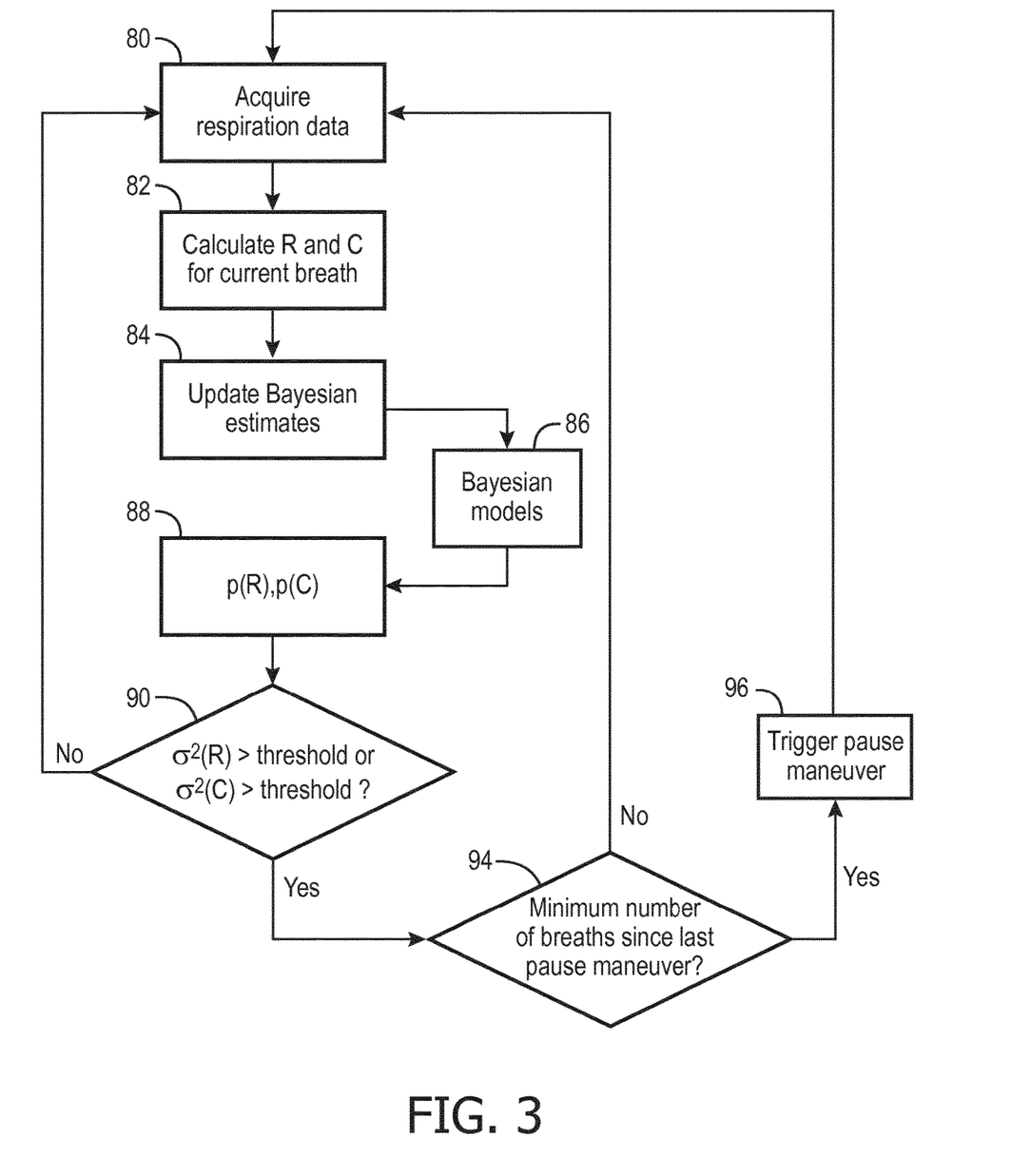
FIG. 3 shows a flow chart of a process for triggering pause maneuvers based on a Bayesian model of the respiratory parameters R and C.

With reference to FIG. 3, process flow of the ventilation device of FIG. 1 in the case in which the respiratory mechanics index 48 is defined in terms of probability density functions for R and C measured under the assumption $P_{mus}(t)=0$ (i.e. passive patient assumption) is described. In an operation 80, respiration data are acquired by the respiratory sensors 30, 32, e.g. (P(t), Q(t)) data pairs, or (P(t), Q(t), V(t)) data triplets if the lung volume V(t) is computed by integrating air flow Q(t). In an operation 82, respiratory resistance R and respiratory compliance C are computed for each breath under a (possibly unrealistic) passive patient assumption, e.g. using Equation (2). Each new datum R and new datum C for the latest breath is a further sample that is used in an operation 84 to update the Bayesian models 86 for R and C so as to update corresponding probability density functions 88, i.e. a respiratory resistance probability density function p(R) and a respiratory compliance (or elastance) probability density function p(C) (or, alternatively, an elastance probability density function p(E)).

A respiratory mechanics index is derived from the probability density functions p(R) and p(C) 88 under the following rationale. If respiratory mechanics index is stable, then R and C as computed in operation 82 should be relatively constant over successive breaths. This is true even if the passive patient assumption used in operation 82 is unrealistic, since if respiratory mechanics index is stable then $P_{mus}(t)$ should be similar from breath to breath, so that the error due to non-zero $P_{mus}(t)$ is stable. A stable value for R and C corresponds to narrow corresponding probability density functions p(R) and p(C). The breadth of these probability density functions may be measured by a suitable distribution parameter such as standard deviation or variance. In FIG. 3, the variances $\sigma^2(R)$ and $\sigma^2(C)$ are computed in operation 90 as the respiratory mechanics index 48 of FIG. 1. If the broadening of the probability density functions as measured by variances $\sigma^2(R)$ and $\sigma^2(C)$ is greater than some threshold (which is suitably empirically chosen using past patient data, and the thresholds may in general be different for R and C), then this indicates a change in respiratory mechanics sufficient to trigger a pause maneuver. In illustrative FIG. 3, a further test 94 corresponding to the further test 74 of FIG. 2 is performed, at which if a minimum number of breaths has not occurred since the last pause maneuver then the next pause maneuver is delayed. Assuming both tests 90, 94 are passed, a pause maneuver is triggered in an operation 96.

Although not explicitly drawn, in another illustrative embodiment Bayesian modeling analogous to that of FIG. 3 may be used to generate a time constant probability density function p(τ) for the time constant τ of the embodiment of FIG. 2, so that the respiratory mechanics index can then be a breadth parameter such as variance $\sigma^2(\tau)$, and a pause maneuver may be triggered if $\sigma^2(\tau)$ is greater than an empirically chosen threshold.

Although not explicitly drawn, in another illustrative embodiment the process flow of FIG. 2 may be employed with block 82 substituted for block 62 of FIG. 2 and the thresholding 70 of FIG. 2 being applied to assess the change in R and/or C over successive breaths to detect a change in respiratory mechanics.

The illustrative embodiments trigger an end-inspiration pause maneuver used to measure respiratory compliance C via Equation (3), and optionally also respiratory resistance R using the estimated C. It will be appreciated that the disclosed approaches can also be used for triggering other pause maneuvers for measuring respiratory parameters, such as an end-expiratory pause maneuver used to measure positive end-expiratory pressure (PEEP). Triggering end-expiratory pause maneuvers using a detected change in estimated respiratory mechanics index provides benefits similar to such triggering of end-inspiration pause maneuvers. In general, the triggered pause maneuver comprises closing at least one of the inhalation valve 38 and the exhalation valve 40 for a pause interval and estimating one or more respiratory system parameters from measurements acquired by the respiratory sensors during or after the pause interval.

In the illustrative embodiments, the respiratory parameters are respiratory resistance R and respiratory compliance C. As is well known, respiratory elastance E is simply the reciprocal of compliance, i.e. E=1/C—accordingly, it is contemplated to substitute respiratory elastance E for respiratory compliance C in any embodiment.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A ventilation device comprising:
    a mechanical ventilator;
    respiratory sensors configured to acquire measurements of respiratory variables including at least measurements of airway pressure and airway flow;
    an electronic processor; and
    a non-transitory storage medium storing instructions readable and executable by the electronic processor to perform a ventilation method including:
        operating the mechanical ventilator to provide mechanical ventilation controlled using measurements acquired by the respiratory sensors,
        performing a pause maneuver comprising closing at least one of an inhalation valve and an exhalation valve for a pause interval;
        estimating a respiratory mechanics index from one or more respiratory system parameters estimated from measurements acquired by the respiratory sensors during or after the pause interval including estimating the respiratory mechanics index by computing a time constant (τ) of a decay or airway flow measured by the respiratory sensors during an exhalation phase of a breath, detecting a change in the estimated respiratory mechanics index including detecting the change in the estimated respiratory mechanics index as a detected change in the time constant computed over successive breaths, and triggering a second pause maneuver in response to the detected change in the estimated respiratory mechanics index including:

triggering the pause maneuver in response to the detected change in the time constant over successive breaths exceeding a threshold indicative of the detected change in the estimated respiratory mechanics index; and storing the computed time constant as an updated threshold when the detected change in the time constant over successive breaths underruns the threshold.

2. The ventilation device of claim 1, wherein the operating the mechanical ventilator to provide mechanical ventilation comprises:

operating the mechanical ventilator to provide mechanical ventilation using a pressure support ventilation (PSV) mode, a proportional assists ventilation (PAV) mode, a synchronized intermittent mandatory ventilation (SIMV) mode, a pressure controlled ventilation (PCV) mode, or a volume controlled ventilation (VCV) mode.

3. The ventilation device of claim 1, wherein the operating of the mechanical ventilator to provide mechanical ventilation is further controlled using the one or more respiratory system parameters estimated from measurements acquired by the respiratory sensors during or after the pause interval.

4. The ventilation device of claim 1, further comprising:
a display;
wherein the one or more respiratory system parameters estimated from measurements acquired by the respiratory sensors during or after the pause interval include a respiratory resistance and a respiratory compliance or elastance;
wherein the ventilation method further includes displaying the respiratory resistance and a respiratory compliance or elastance on the display.

5. A non-transitory storage medium storing instructions readable and executable by an electronic processor to perform operations including:

operating a mechanical ventilator to provide mechanical ventilation, performing a pause maneuver comprising closing at least one of an inhalation valve and an exhalation valve of the mechanical ventilator for a pause interval and estimating one or more respiratory system parameters from airway flow and airway pressure measurements acquired by respiratory sensors during or after the pause interval, monitoring an estimated respiratory mechanics index based on at least one of airway flow and airway pressure measured by respiratory sensors over successive breaths including computing on a per-breath basis, a time constant (τ) of a decay of airway flow during an exhalation phase of the breath, detecting a change in the time constant over successive breaths, and triggering a second pause maneuver in response to detecting a change in the estimated respiratory mechanics index over successive breaths including:

triggering the pause maneuver in response to the detected change in the time constant over successive breaths exceeding a threshold indicative of the detected change in the estimated respiratory mechanics index; and storing the computed time constant as an updated threshold when the detected change in the time constant over successive breaths underruns the threshold.

6. The non-transitory storage medium of claim 1 wherein operating the mechanical ventilator to provide mechanical ventilation comprises:

operating the mechanical ventilator to provide mechanical ventilation using a pressure support ventilation (PSV) mode or a proportional assists ventilation (PAV) mode.

7. The non-transitory storage medium of claim 1 wherein operating the mechanical ventilator to provide mechanical ventilation further comprises adjusting a ventilator setting of the mechanical ventilator based on the one or more respiratory system parameters estimated from measurements acquired by the respiratory sensors during or after the pause interval.

8. A ventilation method including, with an electronic processor:

operating a mechanical ventilator to provide mechanical ventilation;

estimating a respiratory mechanics index over successive breaths during the operating including computing on a per-breath basis, a time constant (τ) if a decay of airway flow measured during an exhalation phase of the breath;

detecting a change in the estimated respiratory mechanics index including detecting flow measured during an exhalation phase of the breath; and triggering a pause maneuver in response to the detected change in the estimated respiratory mechanics index, the pause maneuver comprising closing at least one of an inhalation valve and an exhalation valve of the mechanical ventilator for a pause interval including:

triggering the pause maneuver in response to the detected change in the time constant over successive breaths exceeding a threshold indicative of the detected change in the estimated respiratory mechanics index; and storing the computed time constant as an updated threshold when the detected change in the time constant over successive breaths underruns the threshold; and estimating respiratory compliance from airway measurements acquired during or after the pause interval.

* * * * *